(12) United States Patent
Staudigel

(10) Patent No.: US 10,182,976 B2
(45) Date of Patent: Jan. 22, 2019

(54) PERSONAL CARE COMPOSITION WITH ZINC-CONTAINING LAYERED MATERIAL

(71) Applicant: The Procter & Gamble Company, Cincinnati, OH (US)

(72) Inventor: James Anthony Staudigel, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/448,917

(22) Filed: Mar. 3, 2017

(65) Prior Publication Data

US 2017/0252277 A1    Sep. 7, 2017

Related U.S. Application Data

(60) Provisional application No. 62/303,055, filed on Mar. 3, 2016.

(51) Int. Cl.

| | | |
|---|---|---|
| C07K 16/28 | (2006.01) | |
| A61K 8/27 | (2006.01) | |
| A61K 8/02 | (2006.01) | |
| A61K 8/37 | (2006.01) | |
| A61K 8/44 | (2006.01) | |
| A61K 8/46 | (2006.01) | |
| A61K 8/58 | (2006.01) | |
| A61K 8/73 | (2006.01) | |
| A61K 8/81 | (2006.01) | |
| A61K 8/891 | (2006.01) | |
| A61Q 5/00 | (2006.01) | |

(Continued)

(52) U.S. Cl.
CPC .............. *A61K 8/27* (2013.01); *A61K 8/0245* (2013.01); *A61K 8/0254* (2013.01); *A61K 8/37* (2013.01); *A61K 8/44* (2013.01); *A61K 8/463* (2013.01); *A61K 8/4933* (2013.01); *A61K 8/58* (2013.01); *A61K 8/737* (2013.01); *A61K 8/8158* (2013.01); *A61K 8/891* (2013.01); *A61Q 5/00* (2013.01); *A61Q 5/006* (2013.01); *A61Q 5/02* (2013.01); *A61Q 5/12* (2013.01); *A61K 2800/412* (2013.01); *A61K 2800/524* (2013.01); *A61K 2800/5426* (2013.01); *A61K 2800/58* (2013.01); *A61K 2800/594* (2013.01); *A61K 2800/596* (2013.01); *A61K 2800/651* (2013.01)

(58) Field of Classification Search
CPC . A61K 8/19; A61K 8/23; A61K 33/30; A61K 39/39591; A01N 55/02; C07K 16/2887; C07K 1/14
See application file for complete search history.

(56) References Cited

U.S. PATENT DOCUMENTS

| | | |
|---|---|---|
| 8,343,469 B2 | 1/2013 | Bierganns et al. |
| 8,491,877 B2 | 7/2013 | Schwartz et al. |

(Continued)

OTHER PUBLICATIONS

PCT International Search Report and Written Opinion for PCT/US2017/020602 dated May 12, 2017.

*Primary Examiner* — Carlos A Azpuru
(74) *Attorney, Agent, or Firm* — Linda M. Sivik

(57) ABSTRACT

The present invention is directed to a personal care composition is disclosed comprising: a detersive surfactant from about 2% to 50%; an anti-dandruff active; a cationic polymer; a zinc-containing layered material wherein the zinc-containing layered material has a particle size in the range of from about 0.5 um to 4 um; wherein the ratio of silicone deposition to crystalline structurant deposition is greater than about 5.

17 Claims, 2 Drawing Sheets

(51) Int. Cl.
*A61Q 5/02* (2006.01)
*A61Q 5/12* (2006.01)
*A61K 8/49* (2006.01)

(56) References Cited

U.S. PATENT DOCUMENTS

| | | |
|---|---|---|
| 8,568,701 B2 | 10/2013 | Bierganns et al. |
| 9,381,148 B2 | 7/2016 | Schwartz et al. |
| 2004/0191331 A1 | 9/2004 | Schwartz et al. |
| 2005/0202984 A1 | 9/2005 | Schwartz et al. |
| 2008/0138441 A1 | 6/2008 | Schwartz et al. |
| 2008/0160093 A1 | 7/2008 | Schwartz et al. | ns or methods.
PERSONAL CARE COMPOSITION WITH ZINC-CONTAINING LAYERED MATERIAL

FIELD OF THE INVENTION

The present invention relates to a composition comprising a reduced particle size zinc containing layered material which provides an increase in silicone deposition on hair, as well as a reduction in deposition of structurants, thus providing improved consumer hair conditioning, as well as reduction in buildup residue for an improved clean feel to hair.

BACKGROUND OF THE INVENTION

In current hair care compositions, in particular such compositions comprising anti-dandruff particulates, result in some particulates deposition on both scalp and hair fibers. An effective anti-dandruff shampoo may comprise the combination of zinc pyrithione and zinc carbonate. A typical zinc carbonate particulate may have a particle size distribution with a $D_{50}$ of 5-7 µm. Particles of this size are deposited on hair and this may negatively affects the perception of clean hair feel. Therefore, there is a need to minimize the anti-dandruff particulate impact on hair feel. Surprisingly, the present invention has demonstrated that reducing zinc carbonate particle size results in an increase in silicone deposition on hair and thus an improved consumer hair conditioning experience, as well as a reduction in deposition of structurants, such as ethylene glycol distearate deposition on hair, which in too high amounts leads to buildup, residue and lack of clean feel to hair.

SUMMARY OF THE INVENTION

In an embodiment of the present invention, a personal care composition is disclosed comprising: a detersive surfactant from about 2% to 50%; an anti-dandruff active; a cationic polymer; a zinc-containing layered material wherein the zinc-containing layered material has a particle size in the range of from about 0.5 um to 4 um; wherein the ratio of silicone deposition to crystalline structurant deposition is greater than about 5.

DETAILED DESCRIPTION OF EMBODIMENTS OF THE INVENTION

Figure 1:
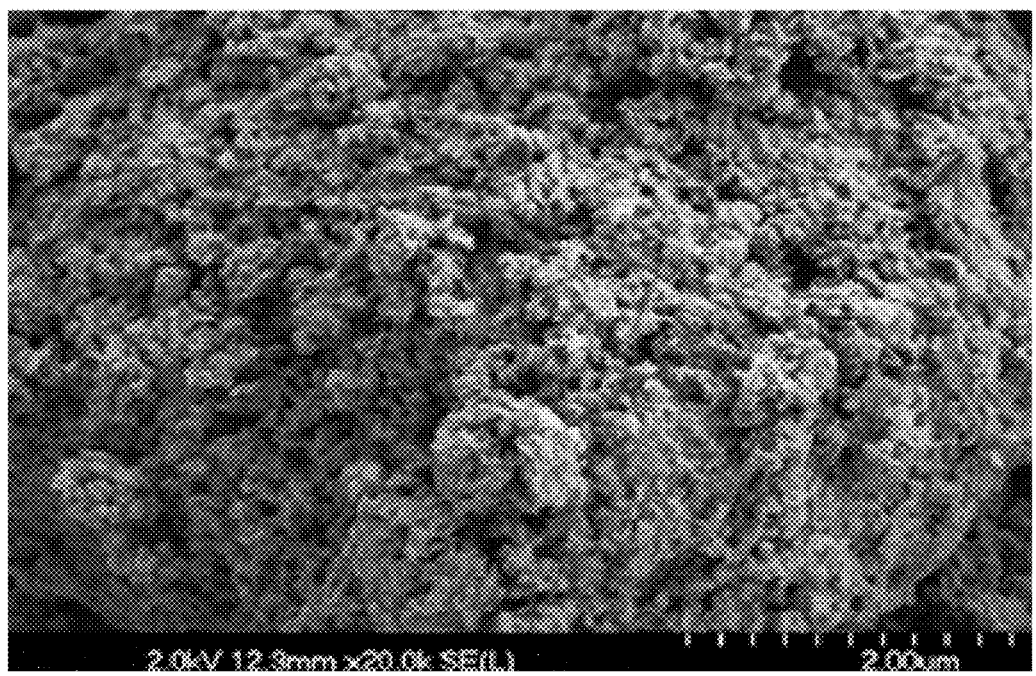
FIG. 1 is an image of Basic Zinc Carbonate A small platelet milled to $D_{50}$ 5-7 µm made via an acidic process.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

In the present invention, three zinc carbonate materials having different particle sizes are evaluated in several shampoo compositions across multiple performance vectors pertaining to in-vivo/vitro cosmetic and efficacy performance. Additionally, physical and chemical evaluations of the zinc carbonate are performed to better understand the composition and morphological characteristics of the material for additional insights into its performance in shampoo and the resulting consumer experience. The present invention demonstrates that as zinc carbonate particle size decreases, silicone deposition on hair fibers increases, while ethylene glycol distearate (EGDS) structurant deposition decreases. In addition, zinc carbonate made via an acidic process possesses a smaller crystal size and, therefore, higher particle surface area compared to zinc carbonate made of a basic process. Increased surface area provides the ability to maximize the potentiation benefits of zinc carbonate when deposited on the scalp in combination with zinc pyrithione (ZPT).

Method of Making Zinc Carbonate: Basic zinc carbonate may be prepared by heating a solution made from anhydrous ammonia and carbon dioxide with added zinc ash in a vessel from 90° C. to 150° C. to produce zinc-ammonia-carbonate complex. The solution is cemented with zinc dust to form a slurry. The slurry is filtered to remove a first precipitate and to produce a first filtrate. The pH of the first filtrate is adjusted to 10 or above to form a second precipitate comprising iron in the first filtrate. The first filtrate is filtered to remove the second precipitate and to produce a second filtrate. At this time magnesium is added if necessary. The pH of the second filtrate is adjusted to below 10 to form a third precipitate comprising zinc carbonate. The zinc carbonate is washed, dried, and milled. (U.S. Pat. No. 6,555,075 Nip) Once the zinc carbonate is washed it exists as a slurry composition and therefore must be dried. The drying process can be via bakery type ovens, spray drying, or similar techniques in order to remove moisture and allow for milling. The milling process may be accomplished via jet milling, pin milling, hammer milling, or similar techniques.

Method of Making Shampoo: The shampoo compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The shampoo composition may be in a single phase or in more than one phase. The insoluble anti-dandruff active, such as ZPT, can be added into the shampoo composition as an aqueous dispersion. The basic zinc carbonate may be added either as a powder or as an aqueous dispersion of the appropriate particle size. Preferably, the basic zinc carbonate is added into a composition having a pH of between 6.7 and 7.3. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

Zinc Carbonate Materials

|  | Basic Zinc Carbonate A | Basic Zinc Carbonate B |
| --- | --- | --- |
| Material Shape | Large Platelet | Small Platelet |
| Making Process | Acidic process | Basic process |

Zinc Carbonate Morphology:

For all the samples observed, regardless of its source, the individual particles appear to be smaller nanoparticles agglomerated together. The overall individual crystal size and shape is guided by the process of making. The morphology remains unchanged across a range of making processes and mechanical particle size reduction.

Figure 2:
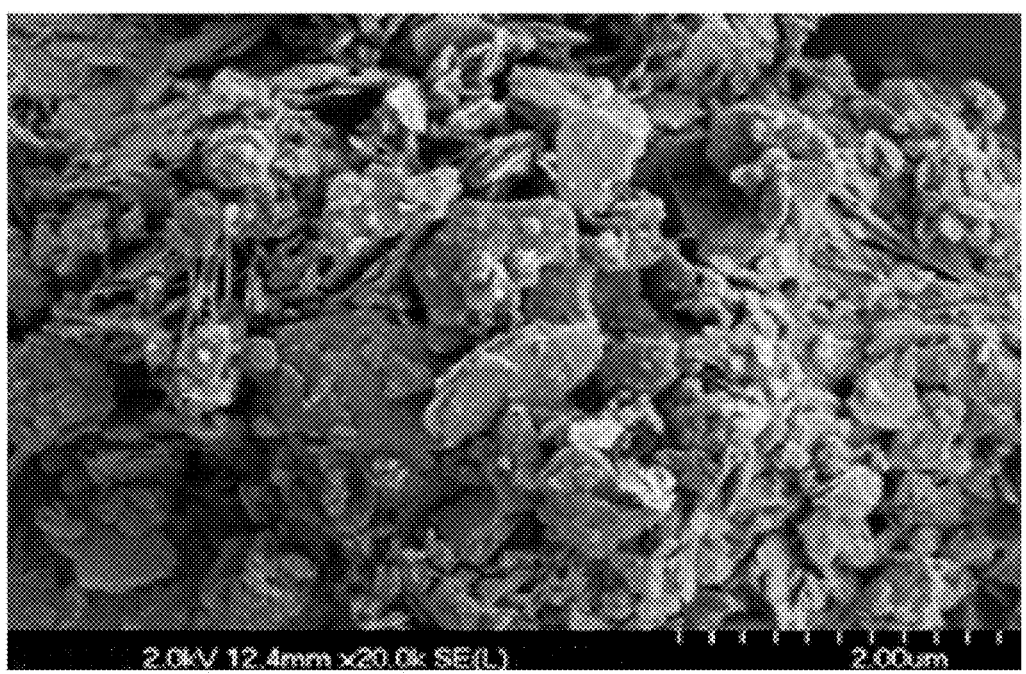
FIG. 2 is an image of Basic Zinc Carbonate B small platelet milled to $D_{50}$ 5-7 µm; made via a basic process.

Basic zinc carbonate A exists in a platelet morphology and average diameter D50 of 5 µm. (FIG. 2) The milling required to reduce the particle size down to 1 micron appears to grind up the plate shaped nanoparticles and reduce their occurrence. Plates appear thick as opposed to the fine and thin basic zinc carbonate B In the case of basic zinc carbonate B, grinding did not appear to disrupt the morphology of the nanoparticles comprising the agglomerates (FIG. 1). It is demonstrated to show a combination of fine plates and irregular particle morphology that is highly agglomerated. Very small plates agglomerated to form larger particles appear to be the prominent morphology of basic zinc carbonate B.

Volume Average Particle Size of Zinc Layered Material

For the purposes of the compositions, formulations and methods described herein, effective particle size is the volume median diameter as determined using laser/light scattering particle size distribution instruments and methods, eg a Horiba LA-950. Similarly, "D90" is the volume-Weighted diameter, wherein 90% of the particles, by volume, have a smaller diameter, while 10% by volume have a larger diameter and "D10" is the volume-Weighted diameter, wherein 10% of the particles, by volume, have a smaller diameter, while 90% by volume have a larger diameter.

A quantity (0.5 g(+/−0.1 g)) of the Zinc Layered Material is dispersed in 150 ml of 1% polyoxyethylene C12-14 ether (eg. LA-7) and mixed for five minutes with a magnetic stir bar. The dispersion is circulated for 2 minutes and the particle volume weighted values are measured after sonication for 2 minutes at standard laboratory temperature. The measurement conditions are transmittance of 90%+/−2%, an ultrasonic treatment for 2 minutes, and the relative refractive index of 1.26.

Without being bound by theory, the present invention has found to have the features of the method according to the first aspect, as well as the other aspects and other relevant components, are described in detail hereinafter. All components of the composition described herein should be physically and chemically compatible with the essential components described herein, and should not otherwise unduly impair product stability, aesthetics or performance.

Deposition Polymer

In an embodiment of the present invention, the shampoo composition may also comprise a cationic deposition polymer. These cationic deposition polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic deposition polymer can be a mixture of deposition polymers.

(1) Cationic Guar Polymers

According to an embodiment of the present invention, the shampoo composition comprises a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

According to one embodiment, the cationic guar polymer has a weight average M.Wt. of less than about 2.5 million g/mol, and has a charge density of from about 0.05 meq/g to about 2.5 meq/g. In an embodiment, the cationic guar polymer has a weight average M.Wt. of less than 1.5 million g/mol, or from about 150 thousand to about 1.5 million g/mol, or from about 200 thousand to about 1.5 million g/mol, or from about 300 thousand to about 1.5 million g/mol, or from about 700,000 thousand to about 1.5 million g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.7 meq/g.

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.7%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

The cationic guar polymer may be formed from quaternary ammonium compounds. In an embodiment, the quaternary ammonium compounds for forming the cationic guar polymer conform to the general formula 1:

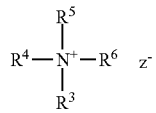

wherein where $R^3$, $R^4$ and $R^5$ are methyl or ethyl groups; $R^6$ is either an epoxyalkyl group of the general formula 2:

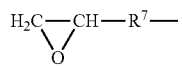

or $R^6$ is a halohydrin group of the general formula 3:

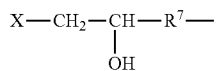

wherein $R^7$ is a $C_1$ to $C_3$ alkylene; X is chlorine or bromine, and Z is an anion such as Cl—, Br—, I— or $HSO_4$—.

In an embodiment, the cationic guar polymer conforms to the general formula 4:

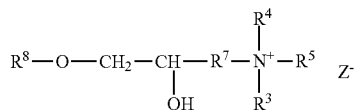

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

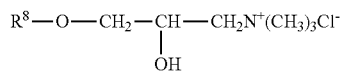

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Jaguar® C-17, which has a cationic charge density of about 0.6 meq/g and a M.Wt. of about 2.2 million g/mol and is available from Rhodia Company. Jaguar® C 13S which has a M.Wt. of 2.2 million g/mol and a cationic charge density of about 0.8 meq/g (available from Rhodia Company). Other suitable guar hydroxypropyltrimonium chloride are: guar hydroxypropyltrimonium chloride which has a charge density of about 1.1 meq/g and a M.Wt. of about 500,000 g/mole is available from ASI, a charge density of about 1.5 meq/g and a M.Wt. of about 500,000 g/mole is available from ASI.

Other suitable guar hydroxypropyltrimonium chloride are: Hi-Care 1000, which has a charge density of about 0.7 meq/g and a M.Wt. of about 600,000 g/mole and is available from Rhodia; N-Hance 3269 and N-Hance 3270, which has a charge density of about 0.7 meq/g and a M.Wt. of about 425,000 g/mole and is available from ASI; N-Hance 3196, which has a charge density of about 0.8 and a M. Wt. Of about 1,100,000 g/mole and is available from ASI. AquaCat CG518 has a charge density of about 0.9 meq/g and a M.Wt. of about 50,000 g/mole and is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

(2) Cationic Non-Guar Galactomannan Polymers

The shampoo compositions of the present invention comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

In one embodiment of the invention, the non-guar galactomannan polymer derivatives have a M. Wt. from about 1,000 to about 10,000,000, and/or form about 5,000 to about 3,000,000.

The shampoo compositions of the present invention include galactomannan polymer derivatives which have a cationic charge density from about 0.5 meq/g to about 7 meq/g. In one embodiment of the present invention, the galactomannan polymer derivatives have a cationic charge density from about 1 meq/g to about 5 meq/g. The degree of substitution of the cationic groups onto the galactomannan structure should be sufficient to provide the requisite cationic charge density.

In one embodiment of the present invention, the galactomannan polymer derivative is a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

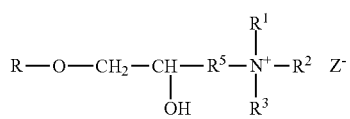

wherein R is the gum. The cationic galactomannan derivative can be a gum hydroxypropyltrimethylammonium chloride, which can be more specifically represented by the general formula 7:

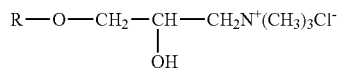

In another embodiment of the invention, the galactomannan polymer derivative is an amphoteric galactomannan polymer derivative having a net positive charge, obtained when the cationic galactomannan polymer derivative further comprises an anionic group.

In one embodiment of the invention the cationic non-guar galactomannan has a ratio of mannose to galactose is greater than about 4:1, a M.Wt. of about 100,000 to about 500,000, and/or from about 150,000 to about 400,000 and a cationic charge density from about 1 meq/g to about 5 meq/g, and/or from 2 meq/g to about 4 meq/g and is a derived from a *cassia* plant.

The shampoo compositions of the present invention comprise at least about 0.05% of a galactomannan polymer derivative by weight of the composition. In one embodiment of the present invention, the shampoo compositions comprise from about 0.05% to about 2%, by weight of the composition, of a galactomannan polymer derivative.

(3) Cationically Modified Starch Polymer

The shampoo compositions of the present invention comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions of the present invention comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the shampoo compositions of the present invention have a molecular weight from about 850,000 to about 15,000,000 and/or from about 900,000 to about 5,000,000. As used herein, the term "molecular weight" refers to the weight average molecular weight. The weight average molecular weight may be measured by gel permeation chromatography ("GPC") using a Waters 600E HPLC pump and Waters 717 auto-sampler equipped with a Polymer Laboratories PL Gel MIXED-A GPC column (Part Number 1110-6200, 600.times.7.5 mm, 20 um) at a column temperature of 55.degree. C. and at a flow rate of 1.0 ml/min (mobile phase consisting of Dimethylsulfoxide with 0.1% Lithium Bromide), and using a Wyatt DAWN EOS MALLS (multi-angle laser light scattering detector) and Wyatt Optilab DSP (interferometric refractometer) detectors arranged in series (using a do/dc of 0.066), all at detector temperatures of 50° C., with a method created by using a Polymer Laboratories narrow dispersed Polysaccharide standard (Mw=47,300), with an injection volume of 200 μl.

The shampoo compositions of the present invention include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers of the present invention generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

In one embodiment of the present invention, cationically modified starch polymers are selected from degraded cationic maize starch, cationic tapioca, cationic potato starch, and mixtures thereof. In another embodiment, cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers in the present invention may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions of the present invention is available from known starch suppliers. Also suitable for use in the present invention is nonionic modified starch that could be further derivatized to a cationically modified starch as is known in the art. Other suitable modified starch starting materials may be quaternized, as is known in the art, to produce the cationically modified starch polymer suitable for use in the invention.

Starch Degradation Procedure: In one embodiment of the present invention, a starch slurry is prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

(4) Cationic Copolymer of an Acrylamide Monomer and a Cationic Monomer

According to an embodiment of the present invention, the shampoo composition comprises a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer comprises:

(i) an acrylamide monomer of the following Formula AM:

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

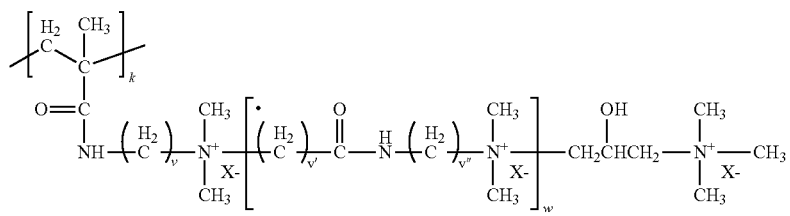

Formula CM where k=1, each of v, v', and v" is independently an integer of from 1 to 6, w is zero or an integer of from 1 to 10, and $X^-$ is an anion.

In an embodiment, cationic monomer conforming to Formula CM and where k=1, v=3 and w=0, z=1 and $X^-$ is $Cl^-$ to form the following structure:

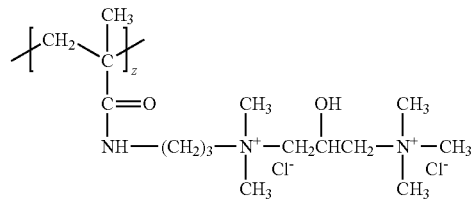

The above structure may be referred to as diquat. In another embodiment, the cationic monomer conforms to Formula CM and wherein v and v" are each 3, v'=1, w=1, y=1 and $X^-$ is $Cl^-$, such as:

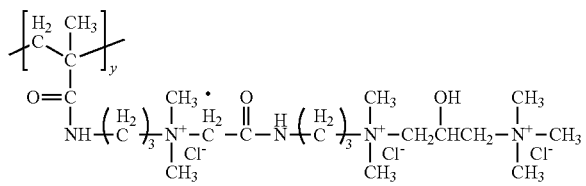

The above structure may be referred to as triquat.

In an embodiment, the acrylamide monomer is either acrylamide or methacrylamide.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;

ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof. In an embodiment, the cationic copolymer comprises a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

In an embodiment, the cationic copolymer is water-soluble. In an embodiment, the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. In an embodiment, the cationized esters of the (meth)acrylic acid containing a quaternized N atom are selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth) acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer based on a (meth)acrylamide is a quaternized dialkylaminoalkyl(meth)acrylamide with C1 to C3 in the alkyl and alkylene groups. In an embodiment, the cationic monomer based on a (meth)acrylamide is dimethylaminopropylacrylamide, which is quaternized with an alkyl halide, especially methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. In an embodiment, the cationic monomer is hydrolysis-stable and the hydrolysis-stable cationic monomer is selected from the group consisting of: diallyldimethylammonium chloride and water-soluble, cationic styrene derivatives.

In an embodiment, the cationic copolymer is a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). In an embodiment, the cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

In an embodiment, the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

In an embodiment, the cationic copolymer has a M.Wt. from about 100 thousand g/mol to about 2 million g/mol, or from about 300 thousand g/mol to about 1.8 million g/mol, or from about 500 thousand g/mol to about 1.6 million g/mol, or from about 700 thousand g/mol to about 1.4 million g/mol, or from about 900 thousand g/mol to about 1.2 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

(5) Cationic Synthetic Polymer

According to an embodiment of the present invention, the shampoo composition comprises a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers In one embodiment, the cationic polymers are water soluble or dispersible, non-crosslinked, and synthetic cationic polymers having the following structure:

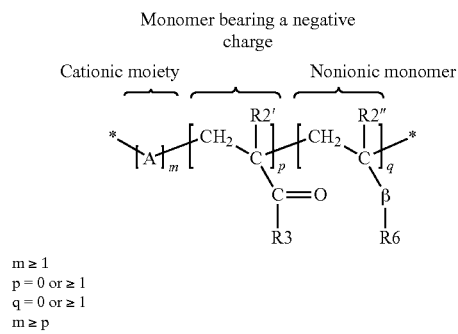

$m \geq 1$
$p = 0$ or $\geq 1$
$q = 0$ or $\geq 1$
$m \geq p$ where A, may be one or more of the following cationic moieties:

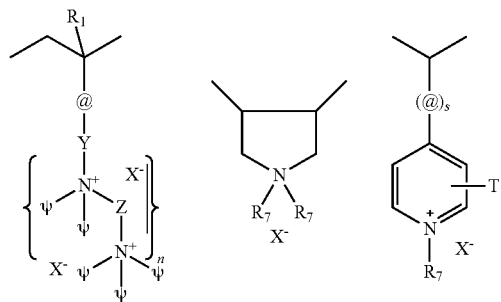

where @=amido, alkylamido, ester, ether, alkyl or alkylaryl;
where $Y$=C1-C22 alkyl, alkoxy, alkylidene, alkyl or aryloxy;
where $\psi$=C1-C22 alkyl, alkyloxy, alkyl aryl or alkyl arylox;
where $Z$=C1-C22 alkyl, alkyloxy, aryl or aryloxy;
where $R1$=H, C1-C4 linear or branched alkyl;
where $s$=0 or 1, $n$=0 or 1;
where T and $R7$=C1-C22 alkyl; and
where $X^-$=halogen, hydroxide, alkoxide, sulfate or alkylsulfate.

Where the monomer bearing a negative charge is defined by $R2'$=H, C1-C4 linear or branched alkyl and $R3$ as:

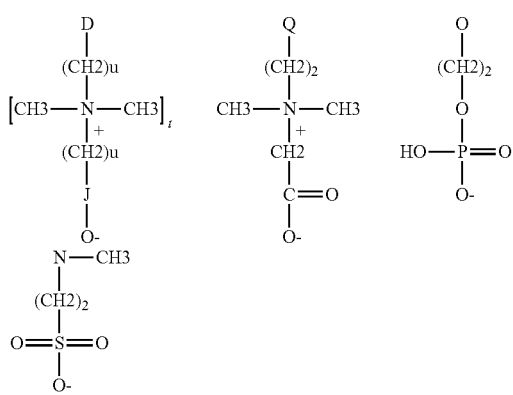

where D=O, N, or S;
where Q=NH$_2$ or O;
where u=1-6;
where t=0-1; and
where J=oxygenated functional group containing the following elements P, S, C.

Where the nonionic monomer is defined by $R2''$=H, C1-C4 linear or branched alkyl, $R6$=linear or branched alkyl, alkyl aryl, aryl oxy, alkyloxy, alkylaryl oxy and β is defined as

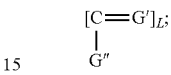

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

In one embodiment, the cationic polymer described herein aids in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable shampoo composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. In some embodiments, the cationic charge density is about 6.2 meq/gm. The polymers also have a M. Wt. of from about 1,000 to about 5,000,000, and/or from about 10,000 to about 2,000,000, and/or from about 100,000 to about 2,000,000.

In another embodiment of the invention cationic synthetic polymers that provide enhanced conditioning and deposition of benefit agents but do not necessarily form lytropic liquid crystals have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 5,000,000, from about 10,000 to about 2,000,000, and from about 100,000 to about 2,000,000.

The concentration of the cationic polymers ranges about 0.025% to about 5%, from about 0.1% to about 3%, and/or from about 0.2% to about 1%, by weight of the shampoo composition.

(6) Cationic Cellulose Polymers

Suitable cationic cellulose polymers are salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

In an embodiment, the shampoo composition comprises a plurality of cationic conditioning polymers. According to one embodiment, where two cationic conditioning polymers are present, the weight ratio of a first cationic conditioning polymer to a second cationic conditioning polymer is from about 1000:1 to about 2:1. In an embodiment, the weight ratio of the first cationic conditioning polymer to the second cationic conditioning polymer is from about 1000:1 to about 4:1. In an embodiment, weight ratio of the first cationic conditioning polymer to the second cationic conditioning polymer is from about 800:1 to about 4:1, or from about 500:1 to about 4:1, or from about 100:1 to about 5:1, or from about 100:1 to about 6:1, or from about 50:1 to about 6.5:1, or from about 50:1 to about 7:1, or from about 50:1 to about 8.3:1, or from about 50:1 to about 16.7:1

The composition comprises an anti-dandruff active, which may be an anti-dandruff active particulate. In an embodiment, the anti-dandruff active is selected from the group consisting of: pyridinethione salts; zinc carbonate; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A.F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+} A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+} 2 \times A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm$^2$. The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm$^2$, or at least about 2.5 microgram/cm$^2$, or at least about 3 microgram/cm$^2$, or at least about 4 microgram/cm$^2$, or at least about 6 microgram/cm$^2$, or at least about 7 microgram/cm$^2$, or at least about 8 microgram/cm$^2$, or at least about 8 microgram/cm$^2$, or at least about 10 microgram/cm$^2$. The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

The composition comprises a cosmetically acceptable carrier. In an embodiment, the carrier is an aqueous carrier. The amount and chemistry of the carrier is selected according to the compatibility with other components and other desired characteristic of the product. In an embodiment, the carrier is selected from the group consisting of: water and water solutions of lower alkyl alcohols. In an embodiment, the carrier is a lower alkyl alcohol, wherein the monohydric alcohol has 1 to 6 carbons. In an embodiment, the carrier is ethanol and/or isopropanol. In an embodiment, the cosmetically acceptable carrier is a cosmetically acceptable aqueous carrier and is present at a level of from about 20% to about 95%, or from about 60% to about 85%.

The composition comprises a surfactant. The surfactant is included to provide cleaning performance to the composition. In an embodiment, the surfactant is selected from the group consisting of: anionic surfactants, amphoteric surfactants, zwitterionic surfactants, cationic surfactants, nonionic surfactants, and mixtures thereof. In an embodiment, the surfactant is an anionic surfactant. In an embodiment, the composition comprises from about 5% to about 50%, or from about 8% to about 30%, or from about 10% to about 25% of a surfactant, by total weight of the composition.

Detersive Surfactant

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

In an embodiment, the co-surfactant is selected from the group consisting of: zwitterionic surfactants, amphoteric surfactants, non-ionic surfactants, and mixtures thereof. In an embodiment, the surfactant is an anionic surfactant and the composition further comprises a co-surfactant, wherein the co-surfactant is selected from the group consisting of: zwitterionic surfactants, amphoteric surfactants, non-ionic surfactants, and mixtures thereof. In an embodiment, the co-surfactant is a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof. In an embodiment, the co-surfactant is a zwitterionic surfactant, wherein the zwitterionic surfactant is selected from the group consisting of: lauryl hydroxysultaine, cocamidopropyl hydroxysultaine, coco-betaine, cocohydroxysultaine, coco-sultaine, lauryl betaine, lauryl sultaine, and mixtures thereof.

Shampoo Gel Matrix

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel matrix surfactants may be any of the detersive surfactants described in section "A" herein.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Structurant

In an embodiment, the present compositions may further comprise a crystalline structurant (or suspending agent), which, when present at concentrations ranging from about 0.05% to about 5%, by weight of the composition, contribute to the phase stability of the composition.

Suitable crystalline structurants include fatty acids or ester derivatives thereof, fatty alcohols, trihydroxystearin (available from Elementis. under the trade name Thixcin. Nonlimiting examples of fatty acids which may be used are C10-C22 acids such as the following: lauric acid, oleic acid, isostearic acid, linoleic acid, linolenic acid, ricinoleic acid, elaidic acid, arichidonic acid, myristoleic acid and palmitoleic acid, and the like. Ester derivatives include ethyleneglycol distearate, propylene glycol isostearate, propylene glycol oleate, glyceryl isostearate, glyceryl oleate, propylene glycol dilaurate and polyglyceryl diisostearate. Preferred are the ethylene glycol stearates, both mono and distearate (EGDS), but particularly the distearate containing less than about 7% of the mono stearate. Other ester derivatives can include long chain esters of long chain fatty acids such as stearyl stearate, cetyl palmitate, lauryl behenate and the like.

Other structurants found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate. Still other suitable nonacyl derivative suspending agents are alkyl(C16-22)dimethyl amine oxides such as stearyl dimethyl amine oxide. Other long chain acyl derivatives suitable for use as structurants include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill. USA).

Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Shampoo Examples

| Ingredient | 1 | 2 | 3 | 4 | 5 | 6 |
|---|---|---|---|---|---|---|
| Cationic guar (1) | 0.23 | 0.23 | 0.23 | 0.23 | 0.23 | 0.23 |
| Cationic guar (2) | | | | | | |
| Sodium Laureth Sulfate (3) | 21.43 | 21.43 | 21.43 | 21.43 | 21.43 | 21.43 |
| Sodium Laureth Sulfate (4) | | | | | | |
| Sodium Lauryl Sulfate (5) | 24.14 | 24.14 | 24.14 | 24.14 | 24.14 | 24.14 |
| PQ-76 (6) | | | | | | |
| AM:APTAC Copolymer (7) | | | | | | |
| PQ-10 (8) | | | | | | |
| Cocoamdopropyl Betaine (9) | 3.33 | 3.33 | 3.33 | 3.33 | 3.33 | 3.33 |
| Cocamide MEA (10) | | | | | | |
| Ethylene Glycol Disterate (11) | 2.5 | 2.5 | 2.5 | 2.5 | 2.5 | 2.5 |
| Dimethicone (12) | 1.7 | 1.7 | 1.7 | 1.7 | 1.7 | 1.7 |
| ZPT (13) | 1.0 | 1.0 | 1.0 | 1.0 | 1.0 | 1.0 |
| Basic Zinc Carbonate A (14) | 1.61 | | | | | |
| Basic Zinc Carbonate A (15) | | | | 1.61 | | |
| Basic Zinc Carbonate A (16) | | | 1.61 | | | |
| Basic Zinc Carbonate B (17) | | | | | 1.61 | |
| Basic Zinc Carbonate B (18) | | 1.61 | | | | |
| Basic Zinc Carbonate B (19) | | | | | | 1.61 |
| Fragrance | 0.75 | 0.75 | 0.75 | 0.75 | 0.75 | 0.75 |
| Sodium Benzoate | 0.25 | 0.25 | 0.25 | 0.25 | 0.25 | 0.25 |
| Preservative (20) | 0.05 | 0.05 | 0.05 | 0.05 | 0.05 | 0.05 |
| Sodium Xylenesulfonate | Quantity necessary to adjust to desired viscosity | | | | | |
| Sodium Chloride | Quantity necessary to adjust to desired viscosity | | | | | |
| Hydrochloric Acid 6N | Quantity necessary to adjust to desired pH | | | | | |
| Water | q.s. | q.s. | q.s. | q.s. | q.s. | q.s. |

| Ingredient | 7 | 8 | 9 | 10 | 11 | 12 |
|---|---|---|---|---|---|---|
| Cationic guar (1) | 0.23 | 0.23 | 0.23 | 0.23 | 0.23 | 0.23 |
| Cationic guar (2) | | | | | | |
| Sodium Laureth Sulfate (3) | 21.43 | 21.43 | 21.43 | 21.43 | 21.43 | 21.43 |
| Sodium Laureth Sulfate (4) | | | | | | |
| Sodium Lauryl Sulfate (5) | 24.14 | 24.14 | 24.14 | 24.14 | 24.14 | 24.14 |
| PQ-76 (6) | | | | | | |
| AM:APTAC Copolymer (7) | | | | | | |
| PQ-10 (8) | | | | | | |
| Cocoamdopropyl Betaine (9) | 3.33 | 3.33 | 3.33 | 3.33 | 3.33 | 3.33 |
| Cocamide MEA (10) | | | | | | |
| Ethylene Glycol Disterate (11) | 2.5 | 2.5 | 2.5 | 2.5 | 2.5 | 2.5 |
| Dimethicone (12) | 0.8 | 0.8 | 0.8 | 0.8 | 0.8 | 0.8 |
| ZPT (13) | 1.0 | 1.0 | 1.0 | 1.0 | 1.0 | 1.0 |
| Basic Zinc Carbonate A (14) | | | | 1.61 | | |
| Basic Zinc Carbonate A (15) | | | | | 1.61 | |
| Basic Zinc Carbonate A (16) | | | | | | 1.61 |
| Basic Zinc Carbonate B (17) | 1.61 | | | | | |
| Basic Zinc Carbonate B (18) | | 1.61 | | | | |
| Basic Zinc Carbonate B (19) | | | 1.61 | | | |
| Fragrance | 0.75 | 0.75 | 0.75 | 0.75 | 0.75 | 0.75 |
| Sodium Benzoate | 0.25 | 0.25 | 0.25 | 0.25 | 0.25 | 0.25 |
| Preservative (20) | 0.05 | 0.05 | 0.05 | 0.05 | 0.05 | 0.05 |
| Sodium Xylenesulfonate | Quantity necessary to adjust to desired viscosity | | | | | |
| Sodium Chloride | Quantity necessary to adjust to desired viscosity | | | | | |
| Hydrochloric Acid 6N | Quantity necessary to adjust to desired pH | | | | | |
| Water | q.s. | q.s. | q.s. | q.s. | q.s. | q.s. |

-continued

| Ingredient | 13 | 14 | 15 | 16 | 17 | 18 |
|---|---|---|---|---|---|---|
| Cationic guar (1) | 0.23 | 0.23 | 0.23 | | | |
| Cationic guar (2) | | | | 0.5 | 0.5 | 0.5 |
| Sodium Laureth Sulfate (3) | 21.43 | 21.43 | 21.43 | 33.9 | 33.9 | 33.9 |
| Sodium Laureth Sulfate (4) | | | | | | |
| Sodium Lauryl Sulfate (5) | 24.14 | 24.14 | 24.14 | 18.97 | 18.97 | 18.97 |
| PQ-76 (6) | 0.02 | | | | | |
| AM:APTAC Copolymer (7) | | 0.005 | 0.01 | | | |
| PQ-10 (8) | | | | | | |
| Cocoamdopropyl Betaine (9) | 3.33 | 3.33 | 3.33 | | | |
| Cocamide MEA (10) | 1.5 | | | 1.6 | 1.6 | 1.6 |
| Ethylene Glycol Disterate (11) | 2.5 | 2.5 | 2.5 | 1.5 | 1.5 | 1.5 |
| Dimethicone (12) | 0.8 | 0.8 | 0.8 | 2.7 | 2.7 | 2. |
| ZPT (13) | 1.0 | 1.0 | 1.0 | 1.0 | 1.0 | 1.0 |
| Basic Zinc Carbonate A (14) | | | | | | |
| Basic Zinc Carbonate A (15) | | | | | | |
| Basic Zinc Carbonate A (16) | | | | | | |
| Basic Zinc Carbonate B (17) | | | | 1.61 | 1.61 | |
| Basic Zinc Carbonate B (18) | 1.61 | 1.61 | 1.61 | | | 1.61 |
| Basic Zinc Carbonate B (19) | | | | | | |
| Fragrance | 0.75 | 0.75 | 0.75 | 0.75 | 0.75 | 0.75 |
| Sodium Benzoate | 0.25 | 0.25 | 0.25 | 0.25 | 0.25 | 0.25 |
| Preservative (20) | 0.05 | 0.05 | 0.05 | 0.05 | 0.05 | 0.05 |
| Sodium Xylenesulfonate | Quantity necessary to adjust to desired viscosity | | | | | |
| Sodium Chloride | Quantity necessary to adjust to desired viscosity | | | | | |
| Hydrochloric Acid 6N | Quantity necessary to adjust to desired pH | | | | | |
| Water | q.s. | q.s. | q.s. | q.s. | q.s. | q.s. |

| Ingredient | 20 | 21 | 22 | a | b | c |
|---|---|---|---|---|---|---|
| Cationic guar (1) | 0.3 | 0.3 | 0.3 | 0.3 | 0.3 | 0.3 |
| Cationic guar (2) | | | | | | |
| Sodium Laureth Sulfate (3) | | | | | | |
| Sodium Laureth Sulfate (4) | 44.23 | 46.15 | 40.38 | 44.23 | 44.23 | 46.15 |
| Sodium Lauryl Sulfate (5) | 5.77 | | 5.77 | 5.77 | 5.77 | |
| PQ-76 (6) | 0.03 | | 0.01 | 0.03 | 0.03 | |
| AM:APTAC Copolymer (7) | | | | | | |
| PQ-10 (8) | | 0.20 | | | | 0.20 |
| Cocoamdopropyl Betaine (9) | 4.17 | 5.00 | 3.33 | 4.17 | 4.17 | 5.00 |
| Cocamide MEA (10) | 2.0 | 1.5 | 1.0 | 2.0 | 2.0 | 1.5 |
| Ethylene Glycol Disterate (11) | 1.5 | 1.5 | 2.5 | 1.5 | 1.5 | 1.5 |
| Dimethicone (12) | 0.8 | 2.2 | 0.8 | 0.8 | 0.8 | 1.0 |
| ZPT (13) | 1.0 | 1.0 | 1.0 | 1.0 | 1.0 | 1.0 |
| Basic Zinc Carbonate A (14) | | | | | | |
| Basic Zinc Carbonate A (15) | | | | | | |
| Basic Zinc Carbonate A (16) | | | | | | |
| Basic Zinc Carbonate B (17) | | | | | | |
| Basic Zinc Carbonate B (18) | 1.61 | 1.61 | 1.61 | 1.61 | 1.61 | 1.61 |
| Basic Zinc Carbonate B (19) | | | | | | |
| Piroctone Olamine (20) | | | | 0.25 | | 0.25 |
| Selenium Sulfide (21) | | | | | 0.25 | |
| Fragrance | 0.75 | 0.75 | 0.75 | 0.75 | 0.75 | 0.75 |
| Sodium Benzoate | 0.25 | 0.25 | 0.25 | 0.25 | 0.25 | 0.25 |

| | | | | | | |
|---|---|---|---|---|---|---|
| Preservative (22) | 0.05 | 0.05 | 0.05 | 0.05 | 0.05 | 0.05 |
| Sodium Xylenesulfonate | Quantity necessary to adjust to desired viscosity | | | | | |
| Sodium Chloride | Quantity necessary to adjust to desired viscosity | | | | | |
| Hydrochloric Acid 6N | Quantity necessary to adjust to desired pH | | | | | |
| Water | q.s. | q.s. | q.s. | q.s. | q.s. | q.s. |

(1) Guar hydroxypropyltrimonium chloride: CD = 0.8 meq./gram, MW = 500,000; supplier Solvay
(2) Guar hydroxypropyltrimonium chloride: CD = 0.8 meq./gram, MW = 425,000; supplier ASI
(3) Sodium Laureth (3M ethylene oxide) Sulfate at 28% active, supplier: P&G
(4) Sodium Laureth (1M ethylene oxide) Sulfate at 26% active, supplier: P&G
(5) Sodium Lauryl Sulfate at 29% active, supplier: P&G
(6) PQ-76, MW = 1,000,000; CD = 1.6 meq./gram; AM:TRIQUAT ratio = 95:5, supplier Solvay
(7) AM/APTAC copolymer (M. Wt. 1.1 million g/mol; charge density 1.8 meq/g), supplier ASI
(8) PQ-10, MW = 2,000,000; CD = 1.25 meq./gram; Polymer JR30M, supplier Dow Chemical
(9) Amphosol HCA from the Stepan Company
(10) Ninol COMF from the Stepan Company
(11) Ethylene Glycol Disterate, supplier: Goldschmidt Chemical
(12) Viscasil 330M from Momentive Performance Materials with a viscosity of 330,000 cSt (centistokes).
(13) Zinc Pyrithione from Lonza
(14) Basic Zinc Carbonate A large platelet milled to $D_{50}$ 5-7 µm; made via acidic process.
(15) Basic Zinc Carbonate A large platelet milled to $D_{50}$ 2.5 µm; made via acidic process.
(16) Basic Zinc Carbonate A large platelet milled to $D_{50}$ 1 µm; made via acidic process.
(17) Basic Zinc Carbonate B small platelet milled to $D_{50}$ 5-7 µm; made via basic process.
(18) Basic Zinc Carbonate B small platelet milled to $D_{50}$ 2.5 µm; made via basic process.
(19) Basic Zinc Carbonate B small platelet milled to $D_{50}$ 1 µm; made via basic process.
(20) Octopirox from Clariant
(20) Selenium Sulphide USP from Eskay Fine Chemicals
(22) Kathon CG from Akzo Nobel Summary of Methods Hair Switch Treatment Method The shampoo product (0.1 cc/g of hair) is applied to hair switch that has been combed, wet, and lightly squeegeed. The switch is milked 50-60 strokes (over 30 seconds), rinsed with stationary "shower" rinse, squeegeed. The application of the product as well as the milking, the rinsing and the squeegeeing is repeated for a 2nd time. The hair switch is dried in heat box for 30 minutes.

The standard water temperature used for this method is 100° F.+/−3° F. and the water hardness is adjusted to 7 grains per gallon (gpg). The water flow is adjusted to 1.5 gallons per minute (gpm)+/−0.25 gpm.

The hair switch is ready for the measurement of the deposition amount of any species of interest.

Silicone Deposition (ii) Silicone Deposition Measurement

The deposited silicone on the hair switch which is treated via the switch treatment method is extracted in an appropriate solvent. The extracts are then introduced into an atomic absorption/emission detector instrument and measured at the appropriate wavelength. The absorbance/emission value returned by the instrument is then converted to actual concentration (ppm) of silicone compound deposited on the hair through an external calibration curve obtained with known weights of a well characterized standard of the silicone compound under study.

Zinc Carbonate Extraction Method:

The zinc carbonate deposited on the hair switch which is treated via the switch treatment method is extracted with a mixture of 20% ethanol in 0.05M EDTA. A portion of the extract is dried under nitrogen and dissolved in a dilute nitric acid solution for total zinc analysis via inductively coupled plasma—optical emission spectroscopy using a yttrium internal standard. Another portion of the ethanol/EDTA extract is prepared for HPLC analysis of zinc pyrithione by adding a solution of 2,2-dithiodipyridine in acetonitrile. The derivatised sample is analyzed by HPLC on a C18 column with a phosphoric acid:acetonitrile (80:20) mobile phase.

The amount of zinc carbonate is calculated as a difference between the total zinc and the zinc from the zinc pyrithione content.

Consumer Product Use Test Method

Male and female panelists in the U.S. and China, ranging in age from 18-65 participate in this usage study. The study is executed and data is collected by an independent marketing research supplier. Research panelists are voluntary participants from the supplier's on-line database and represented a spectrum of ethnicities, hair types and lengths, income levels, household sizes and geographic regions within the U.S. on-line population. The recruitment criteria include a minimum shampoo frequency of 3 times a week (or more) and scalp health concerned or used an antidandruff shampoo in the last three months.

Panelists are given a test shampoo to use in place of their usual products for four weeks. The panelists follow their typical shampoo usage routine throughout the study period. Shampoo dosage and frequency of use is determined by the panelists. The test products are placed in plain white packaging and simply labeled as an "Anti-Dandruff Shampoo" test product. Neither brand nor benefit context are provided. Throughout the study period, panelists are permitted to use their normal conditioner and styling products and follow their typical drying and styling routine. At the end of the study period, a self-administered, on-line survey is completed by each panelist. Study participants are asked to rate the test "Anti-Dandruff Shampoo" on a standard 5 point "Poor to Excellent" scale [100=excellent, 75=Very Good, 50=Good, 25=Fair, 0=Poor], overall and for a series of Hair Care related benefits. The total base size of completed evaluations for each test "Anti-Dandruff Shampoo" is 300 women. All data is then analyzed using standard statistical tests at 90% Confidence and 80% power.

ToF-SIMS Surface Deposition Measurement Method:

Individual hair fibers from hair switches treated via the switch treatment method are analyzed using Time-of-Flight Secondary Ion Mass Spectrometry (ToF-SIMS) to evaluate the amount of active surface deposition on hair surfaces. ToF-SIMS provides semi-quantitative mass spectrum analysis of the outmost 3 nm of the hair surface.

Individual hair fibers are directly mounted onto ToF-SIMS sample holder and pumped into the high vacuum system for surface spectrum analysis. For each hair sample, a ~50×50 μm area is selected along the hair fiber and at least 5 randomly selected hair fibers per hair treatment are used to represent statistics results (average and standard deviation). Characteristic signals from the mass spectrum (positive mode and negative mode analysis) are uniquely selected to represent each of the actives deposited on the hair surface. Semi-quantitative deposition analysis is achieved by normalizing the characteristic signal peak intensity to the total ion intensity in each measurement to avoid fiber size difference and instrument variation from time to time.

Measurement of Zinc Carbonate Surface Area Using Inverse Gas Chromatography Method:

$ZnCO_3$ sample is loaded into 30 cm long×3 mm diameter columns. Samples are first dried in oven for 1 hour at 30° C. The headspace from hydrocarbon, Octane, is injected into the column at 30° C. and nil humidity and retention is determined. Surface area (SA) is determined from Octane retention.

XPS

X-ray photoelectron spectroscopy (XPS) is a surface-sensitive quantitative spectroscopic technique that measures the elemental composition at the parts per thousand range, empirical formula, chemical state and electronic state of the elements that exist within a material. XPS spectra are obtained by irradiating a material with a beam of X-rays while simultaneously measuring the kinetic energy and number of electrons that escape from the top 0 to 10 nm of the material being analyzed. XPS requires high vacuum ($P\sim10^{-8}$ millibar) or ultra-high vacuum (UHV; $P<10^{-9}$ millibar) conditions, although a current area of development is ambient-pressure XPS, in which samples are analyzed at pressures of a few tens of millibar.

XPS Deposition Measures: A thin layer of ZnCO3 particle samples is coated onto a piece of Si wafer covered with double sticky tape and then analyzed using X-ray photoelectron spectroscopy (XPS). XPS provides quantitative elemental composition information (excluding H and He) on the outermost 10 nm of the sample's surface. The particle coated Si wafer surfaces is pumped down in high vacuum system (typical vacuum level for analysis is 10(−8) to 10(−9) torr). 5 points is randomly selected on the particle surfaces for analyses in each sample specimen and average and standard deviation is reported to represent the elemental composition of the particle specimens. The main photoemission peak for each element (e.g. C1s, O1s, Si2p, Zn2p, etc.) is used for semi-quantification after correction using the appropriate sensitivity factor based on the equation below:

$$\text{Atomic \% Element} = \frac{\text{Normalized Peak area for Element}}{\Sigma(\text{Normalized Peak Areas for all elements detected})}$$

$$\text{Normalized Peak Area} = \text{Peak Area}/(\text{Sensitivity Factor} \times \text{Energy Compensation Factor})$$

ICP

Inductively Coupled Plasma—Atomic Emission Spectroscopy (ICP-AES) also known as Inductively Coupled Plasma—Optical Emission Spectroscopy (ICP-OES), measures element-specific spectra emitted from atoms and atomic species in a heated in plasma.

This method is a widely utilized characterization technique for multi-elemental determinations using simultaneous optical systems and axial or radial viewing of the plasma. The instrument measures characteristic emission spectra by optical spectrometry. Samples are nebulized and the resulting aerosol is transported to the plasma torch. Element-specific emission spectra are produced by radio-frequency inductively coupled plasma. The spectra are dispersed by a grating spectrometer, and the intensities of the emission lines are monitored by photosensitive devices. Background correction is required for trace element determination. Background must be measured adjacent to analyte lines on samples during analysis. The position selected for the background-intensity measurement, on either or both sides of the analytical line, will be determined by the complexity of the spectrum adjacent to the analyte line. In one mode of analysis the position used should be as free as possible from spectral interference and should reflect the same change in background intensity as occurs at the analyte wavelength measured. Background correction is not required in cases of line broadening where a background correction measurement would actually degrade the analytical result.

Preparation

Each successful analysis begins by adequately digesting the sample for the analysis in water that is stabilized with acid. The final outcome of each preparation is to afford a homogenous solution of the analyte in the analysis solvent.

Analysis

Sample solutions are infused into the ICP instrument by way of a peristaltic pump. The solution is nebulized into an aerosol that is transported to a plasma torch. Metal ions in the sample solution are subjected to intense heat in a radio-frequency inductively coupled argon plasma. The elements emit characteristic spectra which are separated by a grating. The intensity of the emission lines are monitored by a photosensitive device. Metal ion concentrations of unknown samples are determined by comparison to an external calibration of the instrument.

Measurement of Zinc Carbonate Surface Area Using Brunauer-Emmett_Teller (BET) Surface Area Method:

Zinc Carbonate samples are prepared by heating while simultaneously evacuating or flowing gas over the sample to remove the liberated impurities. The prepared samples are then cooled with liquid nitrogen and analyzed by measuring the volume of $N_2$ gas adsorbed at specific pressures. The specific surface area of $ZnCO_3$ powder is determined by physical adsorption of a gas on the layer on the surface. Physical adsorption results from relatively weak forces (van der Waals forces) between the adsorbate gas molecules and the adsorbent surface area of the test powder. The determination is usually carried out a the temperature of liquid nitrogen. The amount of gas adsorbed can be measured by a volumetric or continuous flow procedure.

Shine Measurement:

Hair from hair switches treated via the switch treatment method switches are mounted to a cylindrical hair holder and presented to an imaging sensor. Images representing the front side reflection, backside reflection, and diffuse reflection are acquired using the method described in "US 2011/0075144 A1". The front and the backside reflection images are summed together to yield a Specular reflection Image. The resulting Specular reflection and Diffuse images are analyzed in the following manner:

1. The region of interest inside the hair area is drawn.
2. From this region of interest, a line profile is extracted in which the pixel columns are averaged together within each of the 3 (RGB) color channels and finally the 3 color channels averaged together for each column of pixels to obtain a single intensity value that represents each column of pixels.
3. The metrics for each line profile included the following:
   Area under the curve (AUC)
   Width at ½ height (W)

The shine parameters are then incorporated in the Reich Robbins shine equation[1] to calculate the overall amount of shine for each hair switch.

1. C. Reich and C. R. Robbins, Light scattering and shine measurements of human hair: A sensitive probe of the hair surface, *J. Soc. Cosmet. Chem.*, 44, 221-234 (1993).

$$RRS = \frac{(Specular\ AUC)}{(Diffuse\ AUC) * (Specular\ W)}$$

Results
Analysis:

There are several unexpected benefits associated with zinc carbonate particle shape and a reduction in particle size from 5-7 µm (to both 2.5 µm and 1 µm).

Comparative Data: Independent Variables

Large base consumer data below shows a surprising statistical consumer preference for 2.5 µm zinc carbonate AND a 0.5% reduction in silicone level in the same shampoo composition. The consumer response is corroborated with TOF-SIMS analysis of hair switches treated with the same compositions which shows an increase in silicone deposition and a reduction in undesired EGDS deposition. In addition, the composition with 2.5µ Zinc carbonate and reduced silicone level shows a statistical increase in hair volume vs both 5 µm and 2.5 µm zinc carbonate compositions with 2.7% silicone (see table I, II & III).

It is also surprising to find that there is statistically more hair shine produced from hair treated with a 1 µm zinc carbonate composition than the same composition containing 5 µm zinc carbonate (see table IV).

TABLE I

Particle Size- Consumer attributes N = 300 respondents

|  | Example 16 | Example 18 |
|---|---|---|
| Particle Size (µm) | 5 | 2.5 |
| Basic zinc carbonate type | Basic zinc carbonate B | Basic zinc carbonate A |
| Silicone Level (%) | 2.7 | 2.2 |
| Leaving my hair feeling clean when dry | 76 | 79* |
| Leaving my hair with volume when hair is dry | 74 | 76* |
| Providing long lasting clean feel | 75 | 77* |
| Removing dandruff flakes | 75 | 77* |
| Feeling confident flakes have been removed | 75 | 77* |
| Feel it work instantly on my scalp | 73 | 75* |
| Providing instant relief from tightness | 72 | 75* |

*statistical significance at 90%

TABLE II

Particle Size- TOF-SIMS of treated hair switches

|  | Blank Hair | Example 2 | Example 1 |
|---|---|---|---|
| Zinc Carbonate Particle size | — | 2.5 µm | 5.0 µm |
| Basic zinc carbonate type |  | Basic zinc carbonate A | Basic zinc carbonate B |
| Silicone Deposition | 0.02 ± 0.003 * | 0.1 ± 0.01 * | 0.05 ± 0.02 * |
| EGDS Deposition | 0.0004 ± 0.00004 * | 0.02 ± 0.005 * | 0.03 ± 0.005 * |

* statistical significance at 90% ± SEM

Characteristic signal peak intensity for silicone (75, 149, and 223) and EGDS (255, 283) is normalized to the total ion intensity in each measurement.

TABLE III

Particle Size- expert panelists (in-vivo hair switch sensory) General Population Hair

|  | Example 16 | Example 18 |
|---|---|---|
| Particle Size (µm) | 5 | 2.5 |
| Basic zinc carbonate type | Basic zinc carbonate B | Basic zinc carbonate A |
| Silicone Level (%) | 2.7 | 2.2 |
| Volume- Dry Feel Sensory | 1.4 | 4.0* |

*statistical significance at 90%

TABLE IV

Particle Shape/Platelet Size- General Population Hair

|  | Example 3 | Example 4 | Example 6 | Example 1 | Example 2 | Example 5 |
|---|---|---|---|---|---|---|
| Particle Shape | Spherical/ small Platelet | Spherical/ small Platelet | Large platelet | Spherical/ small Platelet | Large platelet | Large platelet |
| Basic zinc carbonate type | Basic zinc carbonate B | Basic zinc carbonate B | Basic zinc carbonate A | Basic zinc carbonate B | Basic zinc carbonate A | Basic zinc carbonate A |
| Zinc Carbonate Particle Size (µm) | 1 | 2.5 | 1 | 5 | 2.5 | 5 |

TABLE IV-continued

Particle Shape/Platelet Size- General Population Hair

|  | Example 3 | Example 4 | Example 6 | Example 1 | Example 2 | Example 5 |
|---|---|---|---|---|---|---|
| Zinc Carbonate Depo (ug/cm$^2$) | *899 ± 25 | 752 ± 12 | 766 ± 21 | 663 ± 83 | *740 ± 56 | *579 ± 39 |
| Shine Value | &75 ± 6 | 65 ± 6 | 68 ± 3 | &62 ± 4 | 65 ± 6 | 68 ± 6 |

*statistical significance at 90%
&statistical significance at 95%

TABLE V

Silicone Deposition on Low Lift Damaged Hair Switch (in-vitro)

|  | Example 6 | Example 3 |
|---|---|---|
| Zinc Carbonate Particle Shape | Large-platelet | Small platelet |
| Basic zinc carbonate type | Basic zinc carbonate A | Basic zinc carbonate B |
| Particle Size (D$_{50}$) in μm | 1 | 1 |
| Silicone Deposition in ppm | 35 ± 9 | 15 ± 6 |

Surface Area by IGC Acidic Process

|  | Material 17 | Material 18 | Material 19 |
|---|---|---|---|
| Particle Shape | Small platelet | Small platelet | Small platelet |
| Basic zinc carbonate type | Basic zinc carbonate B | Basic zinc carbonate B | Basic zinc carbonate B |
| Particle Size (D$_{50}$) in μm | 5 | 2.5 | 1 |
| Surface Area (m$^2$/g) IGC | 55 | 67 | — |

Surface Area by IGC—Basic Process

|  | Material 14 | Material 15 | Material 16 |
|---|---|---|---|
| Particle Shape | Large platelet | Large platelet | Large platelet |
| Basic zinc carbonate type | Basic zinc carbonate A | Basic zinc carbonate A | Basic zinc carbonate A |
| Particle Size (D$_{50}$) in μm | 5 | 2.5 | 1 |
| Surface Area (m$^2$/g) IGC | 28 | 42 | 48 |

Chemistry (Destructive Elemental)

|  | Materials 14-16 average | Materials 17-19 average |
|---|---|---|
| Making Process | Basic | Acidic |
| Basic zinc carbonate type | Basic zinc carbonate A | Basic zinc carbonate B |
| Zn2+ (% wt) | 55 | 58 |
| Mg2+ (% wt) | 2.5 | 1.4 |
| Crystallinity (Angstroms) | 100 | 95 |
| ZnO (% wt) | <1 | 6 |
| Particle Size | Various (17-19) | Various (14-16) |
| Surface Area (m$^2$/g) IGC avg | 39 | 61 |
| Surface Area (m$^2$/g) BET avg | 20 | 40 |

Surface Chemistry (Outer 10 nm Elemental)

|  | Materials 14-16 average | Materials 17-19 average |
|---|---|---|
| Making Process | Basic | Acidic |
| Basic zinc carbonate type | Basic zinc carbonate A | Basic zinc carbonate B |
| Zn2p (%) | 7.3 ± 1.1 | 5.8 ± 1.4 |
| Mg1s (%) | 1.1 ± 0.2 | 0.6 ± 0.1 |
| Crystallinity | 100 | 95 |
| ZnO | <1 | 6 |
| Particle Size | various | various |
| Surface Area (m$^2$/g) IGC avg | 39 | 61 |
| Surface Area (m$^2$/g) BET avg | 20 | 40 |

Examples/Combinations

A. A personal care composition comprising:
   a) a detersive surfactant from about 2% to 50%;
   b) an anti-dandruff active;
   c) a cationic polymer;
   d) a zinc-containing layered material wherein the zinc-containing layered material has a particle size in the range of from about 0.5 um to 4 um; wherein the ratio of silicone deposition to a crystalline structurant deposition is greater than about 5.

B. A personal care composition according to Paragraph A, wherein the composition provides at least a 30% reduction in crystalline structurant deposition on hair when compared to a composition comprising a 5 micron zinc-containing layered material;

C. A personal care composition according to Paragraph A-B, wherein the composition provides at least a 40% reduction in crystalline structurant deposition on hair when compared to a composition comprising a 5 micron zinc-containing layered material;

D. A personal care composition according to Paragraph A-C, wherein the composition provides at least a 50% reduction in a crystalline structurant deposition on hair when compared to a composition comprising a 5 micron zinc-containing layered material;

E. A personal care composition according to Paragraph A-D, wherein the crystalline structurant is selected from the group consisting of fatty alcohols, trihydroxystearin lauric acid, oleic acid, isostearic acid, linoleic acid, linolenic acid, ricinoleic acid, elaidic acid, arichidonic acid, myristoleic acid and palmitoleic acid, ethyleneglycol distearate, propylene glycol isostearate, propylene glycol oleate, glyceryl isostearate, glyceryl oleate, propylene glycol dilaurate and polyglyceryl diisostearate, ethylene glycol monostearate, ethylene glycol distearate, stearyl stearate, cetyl palmitate, lauryl behenate, stearic monoethanolamide, stearic diethanolamide, stearic monoisopropanolamide, stearic monoethanolamide stearate, stearyl dimethyl amine oxide, N,N-dihydrocarbyl amido benzoic acid and soluble salts thereof, N,N-di(hydrogenated) C16, C18 and tallow amido benzoic acid, and mixtures thereof.

F. A personal care composition according to Paragraph A-E, wherein the crystalline structurant if ethylene glycol distearate.

G. A personal care composition according to Paragraph A-F, wherein the composition provides a 2 fold increase in silicone deposition on hair when compared to a composition comprising a 5 micron zinc-containing layered material;

H. A personal care composition according to Paragraph A-G, the zinc-containing layered material has a particle size in the range of from about 0.8 um to about 3.5 um.

I. A personal care composition according to Paragraph A-H, the zinc-containing layered material has a particle size in the range of from about 1 um to about 2.5 um.

J. A personal care composition according to Paragraph A-I, wherein the ratio of silicone deposition to ethylene glycol distearate deposition on hair is greater than about 10.

K. A personal care composition according to Paragraph A-J, wherein the ratio of silicone deposition to ethylene glycol distearate deposition on hair is greater than about 20.

L. A personal care composition according to Paragraph A-K, wherein the composition provides a zinc carbonate deposition on hair in range of from about 300 to about 3000 ug/gram of hair.

M. A personal care composition according to Paragraph A-L, wherein the composition provides a zinc carbonate deposition on a scalp in the range of from about 1 mg/cm$^2$ to about 15 mg/cm$^2$ N. A personal care composition according to Paragraph A-M, wherein the anti-dandruff active is selected from the group consisting of pyrithione salts or metal salts of pyrithione.

O. A personal care composition according to Paragraph A-N, wherein the anti-dandruff active is zinc pyrithione.

P. A personal care composition according to Paragraph A-O, wherein the personal care composition further comprises an anti-dandruff active selected from the group consisting of an azole, octopirox, selenium sulfide, and mixtures thereof.

Q. A personal care composition according to Paragraph A-P, wherein the cationic polymer is selected from the group consisting of a cationic guar polymer, a cationic non-guar galactomannan polymer, a cationic tapioca polymer, a cationic copolymer of acrylamide monomers and cationic monomers, a synthetic, non-crosslinked, cationic polymer, a cationic cellulose polymer, and mixtures thereof.

R. A method for achieving hair smoothing wherein the composition of Paragraph A-Q is applied to the hair.

S. A method of achieving hair shine wherein the composition of Paragraph A-R is applied to the hair.

T. A method of achieving hair volume wherein the composition of Paragraph A-S is applied to the hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A personal care composition comprising:
   a) a detersive surfactant from about 2% to 50%;
   b) an anti-dandruff active;
   c) a cationic polymer;
   d) a zinc-containing layered material made by a basic process wherein the zinc-containing layered material has a particle size in the range of from about 0.5 um to 4 um; wherein the ratio of silicone deposition to a crystalline structurant deposition is greater than about 5.

2. A personal care composition according to claim 1, wherein the composition provides at least a 30% reduction in crystalline structurant deposition on hair when compared to a composition comprising a 5 micron zinc-containing layered material.

3. A personal care composition according to claim 1, wherein the composition provides at least a 40% reduction in crystalline structurant deposition on hair when compared to a composition comprising a 5 micron zinc-containing layered material.

4. A personal care composition according to claim 1, wherein the composition provides at least a 50% reduction in a crystalline structurant deposition on hair when compared to a composition comprising a 5 micron zinc-containing layered material.

5. A personal care composition according to claim 1, wherein the crystalline structurant is selected from the group consisting of fatty alcohols, trihydroxystearin lauric acid, oleic acid, isostearic acid, linoleic acid, linolenic acid, ricinoleic acid, elaidic acid, arichidonic acid, myristoleic acid and palmitoleic acid, ethyleneglycol distearate, propylene glycol isostearate, propylene glycol oleate, glyceryl isostearate, glyceryl oleate, propylene glycol dilaurate and polyglyceryl diisostearate, ethylene glycol monostearate, ethylene glycol distearate, stearyl stearate, cetyl palmitate, lauryl behenate, stearic monoethanolamide, stearic diethanolamide, stearic monoisopropanolamide, stearic monoethanolamide stearate, stearyl dimethyl amine oxide, N,N-dihydrocarbyl amido benzoic acid and soluble salts thereof, N,N-di(hydrogenated) C16, C18 and tallow amido benzoic acid, and mixtures thereof.

6. A personal care composition according to claim 5, wherein the crystalline structurant if ethylene glycol distearate.

7. A personal care composition according to claim 1, wherein the composition provides a 2 fold increase in silicone deposition on hair when compared to a composition comprising a 5 micron zinc-containing layered material.

8. A personal care composition according to claim 1 the zinc-containing layered material has a particle size in the range of from about 0.8 um to about 3.5 um.

9. A personal care composition according to claim 1 the zinc-containing layered material has a particle size in the range of from about 1 um to about 2.5 um.

10. A personal care composition according to claim 1, wherein the ratio of silicone deposition to ethylene glycol distearate deposition on hair is greater than about 10.

11. A personal care composition according to claim 1, wherein the ratio of silicone deposition to ethylene glycol distearate deposition on hair is greater than about 20.

12. A personal care composition according to claim 1 wherein the composition provides a zinc carbonate deposition on hair in range of from about 300 to about 3000 ug/gram of hair.

13. A personal care composition according to claim 1 wherein the composition provides a zinc carbonate deposition on a scalp in the range of from about 1 mg/cm$^2$ to about 15 mg/cm$^2$.

14. A personal care composition according to claim 1, wherein the anti-dandruff active is selected from the group consisting of pyrithione salts or metal salts of pyrithione.

15. A personal care composition according to claim 1 wherein the anti-dandruff active is zinc pyrithione.

16. A personal care composition according to claim 1 wherein the personal care composition further comprises an anti-dandruff active selected from the group consisting of an azole, octopirox, selenium sulfide, and mixtures thereof.

17. A personal care composition according to claim 1, wherein the cationic polymer is selected from the group consisting of a cationic guar polymer, a cationic non-guar galactomannan polymer, a cationic tapioca polymer, a cationic copolymer of acrylamide monomers and cationic monomers, a synthetic, non-crosslinked, cationic polymer, a cationic cellulose polymer, and mixtures thereof.

* * * * *